United States Patent

Winter

[11] Patent Number: 5,884,623
[45] Date of Patent: Mar. 23, 1999

[54] SPRING PILOTED SAFETY VALVE WITH JET VENTURI BIAS

[75] Inventor: David P. Winter, Encinitas, Calif.

[73] Assignee: Nellcor Puritan Bennett Incorporated, Pleasanton, Calif.

[21] Appl. No.: 115,380

[22] Filed: Jul. 14, 1998

Related U.S. Application Data

[63] Continuation of Ser. No. 818,104, Mar. 13, 1997, Pat. No. 5,791,339.

[51] Int. Cl.$^6$ ........................................................ A62B 9/02
[52] U.S. Cl. ................................. 128/205.24; 128/202.22
[58] Field of Search ........................ 128/202.22, 204.19, 128/205.24; 251/129.16, 129.2; 137/484.6

[56] References Cited

U.S. PATENT DOCUMENTS

| | | | |
|---|---|---|---|
| 1,848,031 | 3/1932 | Spencer | 137/484.6 |
| 2,331,503 | 10/1943 | Ray | 251/129.16 |
| 2,502,256 | 3/1950 | Harding, Jr. | 251/129.2 |
| 3,039,481 | 6/1962 | Schreiber et al. | 128/204.19 |
| 3,621,867 | 11/1971 | Stang, Jr. | 137/484.8 |
| 3,773,071 | 11/1973 | Stang, Jr. | 137/484.8 |
| 3,906,934 | 9/1975 | Haverland | 128/202.22 |
| 4,142,683 | 3/1979 | Casey et al. | 251/129.2 |
| 4,205,593 | 6/1980 | Sakakibara | 251/129.2 |
| 4,688,565 | 8/1987 | Kobayashi | 128/204.19 |
| 4,838,257 | 6/1989 | Hatch | 128/204.19 |
| 4,840,193 | 6/1989 | Schiel | 251/129.2 |
| 4,869,462 | 9/1989 | Logie et al. | 251/129.16 |
| 4,991,576 | 2/1991 | Henkin et al. | 128/205.24 |
| 5,127,400 | 7/1992 | DeVries et al. | 128/205.24 |
| 5,199,392 | 4/1993 | Kreuter et al. | 251/129.16 |
| 5,273,031 | 12/1993 | Olsson et al. | 128/204.18 |
| 5,339,807 | 8/1994 | Carter | 128/205.24 |
| 5,507,282 | 4/1996 | Younes | 128/205.24 |
| 5,568,910 | 10/1996 | Koehler et al. | 128/205.24 |
| 5,596,984 | 1/1997 | O'Mahony et al. | 128/205.24 |
| 5,687,709 | 11/1997 | Akerberg | 128/205.24 |
| 5,699,788 | 12/1997 | Lekholm et al. | 128/205.24 |
| 5,791,339 | 8/1998 | Winter | 128/202.22 |

*Primary Examiner*—Aaron J. Lewis
*Attorney, Agent, or Firm*—Fulwider Patton Lee & Utecht, LLP

[57] ABSTRACT

The lung ventilator safety valve includes a valve housing, an armature connected to the valve housing, a shaft mounted at one end to the armature and having a poppet valve seal on the other end for sealing the vent in a valve closed position and for allowing a relief flow in a valve open position. An electromagnetic coil mounted to the valve housing adjacent to the armature when energized urges the armature to the armature closed position, and a return spring urges the armature to an open position. The poppet valve seal has an aperture extending through the poppet valve seal, so that when there is relief flow through the safety valve vent, the relief flow across the poppet valve seal creates a jet venturi effect to cause a negative pressure on the side of the poppet valve seal opposite the relief flow that biases the safety valve to open further.

6 Claims, 2 Drawing Sheets

SPRING PILOTED SAFETY VALVE WITH JET VENTURI BIAS

This application is a continuation of Ser. No. 08/818,104, filed Mar. 13, 1997 now U.S. Pat. No. 5,791,339.

BACKGROUND OF THE INVENTION

1. Field of the Invention

This invention relates generally to breathing ventilators, and more particularly concerns a spring piloted safety valve for a lung ventilator that provides ventilation pressure relief when ventilation pressure exceeds a maximum pressure limit, and that provides an emergency path through the safety valve to allow the patient to breathe in the event the ventilator become inoperative for some reason.

2. Description of Related Art

Medical ventilators are generally designed to ventilate a patient's lungs with breathing gas to assist a patient in breathing when the patient is somehow unable to adequately breath without assistance. For inspiration, common ventilators use positive pressure to initiate gas flow into the lungs, while exhalation occurs passively. Typically, inspiratory pressure is controlled through a closed loop inspiratory valve control. To prevent gas from escaping and to provide primary over pressure protection, an exhalation valve is set to a preselected maximum ventilation pressure.

In the event that a system failure occurs, a secondary pressure relief valve is commonly used to limit potentially damaging pressure in the lungs. Pressure relief valves used in this matter are commonly known as safety valves. Most safety valves are set to provide pressure relief at a fixed pressure which is higher than the maximum ventilation pressure, yet low enough to meet maximum pressure limits as set by regulatory agencies.

A feature common to safety valves is that they are pneumatically normally open. In the event of power loss, this gives a spontaneously breathing patient the ability to draw ambient air in through the safety valve.

One known ventilator system includes a safety valve comprising a pivotal plate with an adjustable sealing poppet that fits over the valve opening. Springs are connected to the plate to pull the sealing poppet to cover the valve opening. A spring loaded piston is biased against an end of the plate by a spring to exert a torque pivoting the plate to open the safety valve. An electromagnet pulls the piston against the force of the spring loading to allow the valve to close, and when power to the safety valve is interrupted, the valve is allowed to open. The safety valve opens when excessive pressure accumulates in the inspiration section, at a preprogrammed overpressure, and acts as an emergency valve, opening in the event of a power failure, to provide the patient with air through the open safety valve. However, the air path to the patient in the event of power failure with such a system is relatively restricted.

In the event of ventilator over pressure conditions, it would be desirable to provide a pneumatic system for further opening the safety valve, to thereby more rapidly reduce excess patient pressure, thus lowering the risk of barotrauma. It would also be desirable to provide additional safety by reducing patient pressure as flow increases, to have the ability to tune the valve's pressure relief response time, and to dampen oscillations. The present invention meets these needs.

SUMMARY OF THE INVENTION

Briefly, and in general terms, the present invention provides for an improved lung ventilator safety valve that provides an emergency alternative pathway allowing a patient to breathe in a failure condition of the ventilator, such as when there is an interruption of power to the ventilator, and that relieves patient pressure in excess of a predetermined level during ventilator operation. These advantages are provided by a pneumatic system that additionally utilizes a jet venturi effect to open the safety valve in response to relief flow for rapid reduction of excess patient pressure in order to reduce the risk of barotrauma, and that dampens oscillations of the valve.

The invention accordingly provides for a lung ventilator safety valve for relieving pressure from a vent in a patient airway of a ventilator system. The safety valve includes a valve housing adapted to be mounted to the vent in the patient airway, and armature mounted to the valve housing for movement with respect to the valve housing. A shaft is disposed in the valve housing, the shaft being mounted at one end to the armature and having a poppet valve diaphragm disposed on the other end of the shaft adjacent to a valve seat on the vent for allowing a relief flow from the vent in a valve open position and for sealing the vent in a valve closed position. A pilot spring disposed on the shaft provides a biasing force urging the poppet valve diaphragm to the valve closed position to seal the vent, and a pilot spring adjuster is disposed in the valve housing for adjusting the biasing force of the pilot spring. The poppet valve diaphragm allows relief flow when pressure within the patient airway exceeds the biasing force of the pilot spring, to protect a patient from excess pressure in the patient airway.

An electromagnetic coil or solenoid is also mounted to the valve housing adjacent to the armature. When energized, the electromagnetic coil provides a biasing force that urges the armature to the armature closed position, and a return spring disposed in the valve housing provides a biasing force opposed to the biasing forces of the pilot spring and the electromagnetic coil. The biasing force of the return spring is less than the biasing force of the electromagnetic coil, and is greater than the biasing force of the pilot spring. Thus, when the electromagnetic coil is energized, the operation of the valve depends upon the balance of forces of the pilot spring and the patient airway pressure, and when the electromagnetic coil is not energized, such as would be the case if there is interruption of power to the ventilator, the return spring causes the safety valve to open to provide an emergency air pathway for the patient.

In a presently preferred embodiment, the poppet valve diaphragm is also formed with a small aperture extending through the poppet valve diaphragm, so that when there is relief flow through the safety valve vent, the relief flow across the valve poppet diaphragm creates a jet venturi effect producing a negative pressure on the side of the diaphragm opposite the relief flow, to bias the safety valve to open further, reducing patient pressure further and reducing the risk of barotrauma to the patient.

These and other aspects and advantages of the invention will become apparent from the following detailed description and the accompanying drawings, which illustrate by way of example the features of the invention.

DETAILED DESCRIPTION OF THE PREFERRED EMBODIMENTS

While conventional ventilators typically have limited ventilator pressure to a maximum by a pressure relief valve or safety valve with a fixed maximum rated pressure, it is also important to relieve excessive pressure buildup rapidly, to prevent harm to a patient's lungs by a higher than desirable pressure in the lungs. It is also possible for oscillations of a ventilator safety valve during relief flow to result in overpressure oscillations, so that it is important to dampen such pressure oscillations during relief flow. Furthermore, when the ventilator is turned off, or otherwise fails to operate such as in the event of a power failure, an emergency airway vent must be provided to allow the patient to breathe on his or her own when the ventilator is not operating.

Figure 1:
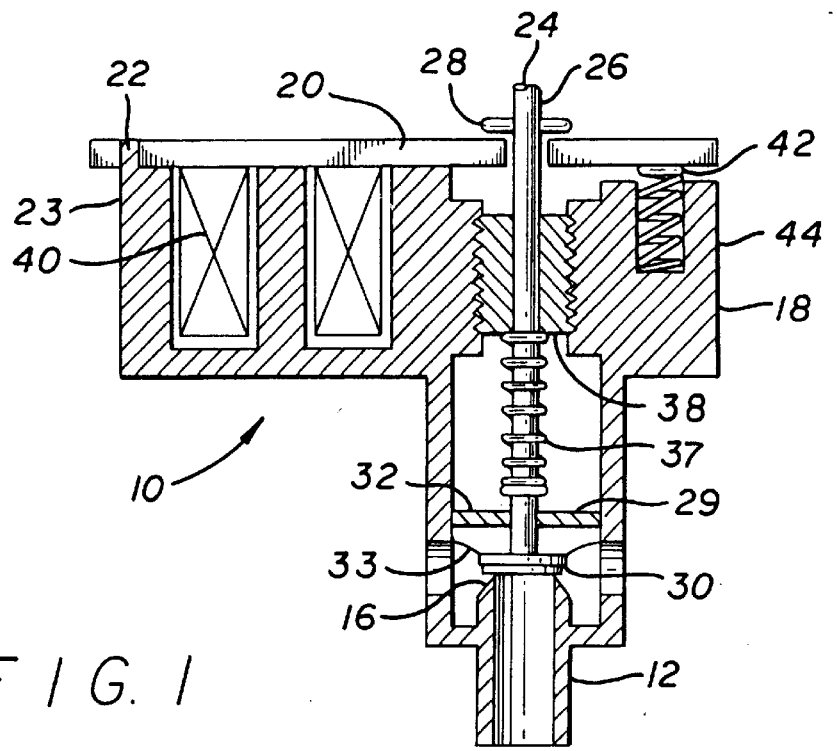
FIG. 1 is a schematic elevational sectional view of the lung ventilator safety valve of the invention, showing the armature and valve in closed positions.
Figure 2:
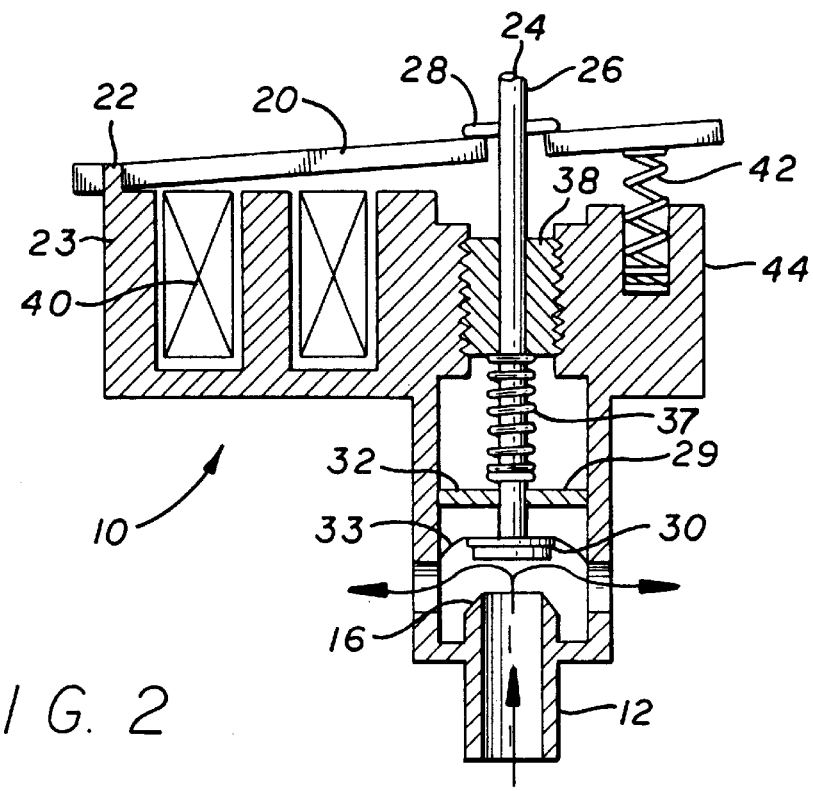
FIG. 2 is a schematic elevational sectional view of the lung ventilator safety valve similar to that of FIG. 1, showing the armature and valve in open positions.

As is illustrated in the drawings, the invention is embodied in a lung ventilator safety valve 10 for relieving pressure through a vent 12 in a patient airway (now shown) of a ventilator system. The vent is provided with a valve seat 16, and the safety valve has a valve closed position preventing relief flow through the vent, and a valve open position venting pressure from the patient airway. In a currently preferred embodiment, as is illustrated in FIGS. 1 and 2, the safety valve has a valve housing 18 mounted to the vent of the patient airway, and an armature 20 mounted to the valve housing, preferably by a hinge 22 at one end 23 of the valve housing, for movement with respect to the valve housing, between an armature open position and an armature closed position. A shaft 24 is disposed in the valve housing and is loosely mounted at one end 26 of the shaft to the armature by a retaining washer 28. The shaft extends through a housing shaft guide 29, mounted within the housing, to guide the movement of the shaft and the poppet valve seal. A poppet valve seal 30 is mounted to the other end 32 of the shaft adjacent to and adapted to seal the valve seat of the vent for sealing the vent in the valve closed position, as shown in FIG. 1, and for allowing a relief flow from the vent in the valve open position, as shown in FIG. 2. As is also shown more clearly in FIG. 3, the poppet valve seal also includes a flexible diaphragm 33 extending to the valve housing around the poppet valve seal, as will be further explained below.

Figure 3:
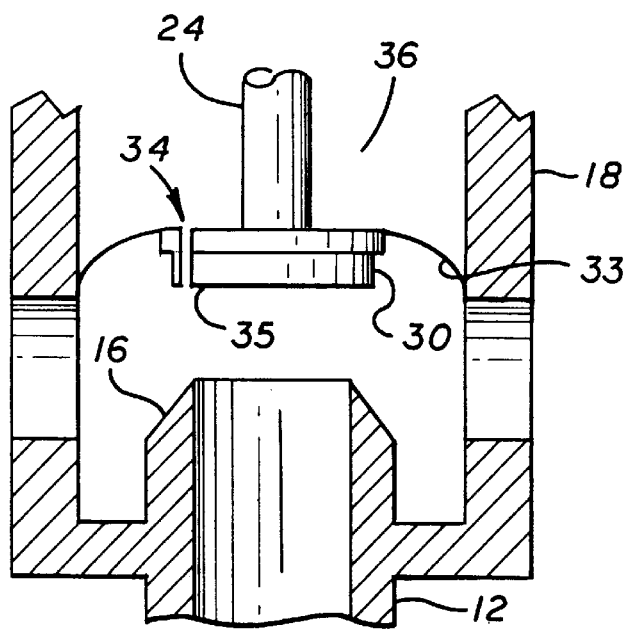
FIG. 3 is an enlarged partial sectional view of the poppet valve seal of the ventilator safety valve of FIGS. 1 and 2 illustrating the jet venturi effect of the aperture in the poppet valve seal during relief flow.

With reference to FIG. 3, the poppet valve seal has a narrow aperture 34 extending through the poppet valve seal at a location on the poppet valve seal outside the vent so as to not be in communication with the vent when the poppet valve seal is seated on the vent. In a currently preferred embodiment, the aperture through the poppet valve seal is laser drilled. As can be seen in FIG. 3, when there is relief flow out through the safety valve vent, the relief flow across lower surface 35 of the valve poppet diaphragm creates a jet venturi effect through the narrow aperture communicating with the chamber 36 in the housing formed by the walls of the housing, and the poppet valve seal and flexible diaphragm, resulting in a negative pressure on the opposing side of the poppet valve seal in the chamber 36 in the housing that biases the safety valve to open further.

Figure 4:
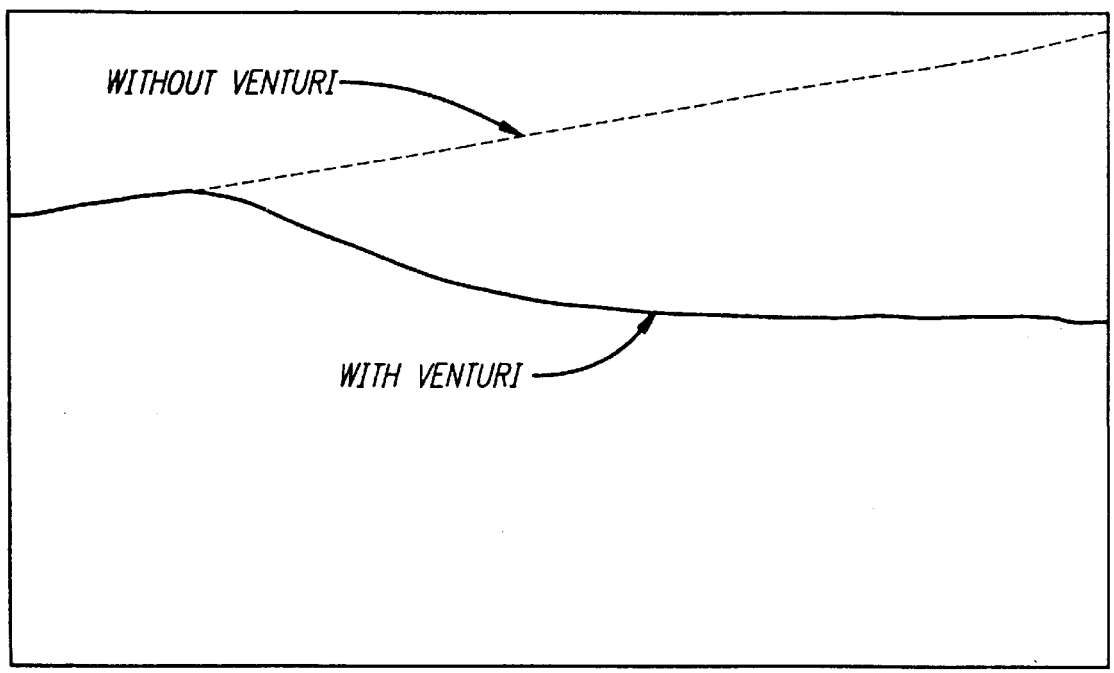
FIG. 4 is a graph illustrating the negative pressure trace of the safety valve of the invention due to the jet venturi effect created by the poppet valve seal aperture, in comparison with a normal pressure trace of a safety valve without a jet venturi aperture in the poppet valve seal, in relation to an increase in relief flow.

In conventional spring operated safety relief valves, during pressure relief, the patient pressure acts against the pilot spring to open the valve to allow relief flow, and patient pressure is generally proportional to the relief valve flow, so that the pressure experienced by the patient will generally increase with the flow rate during pressure relief, typically resulting in the upper pressure vs. flow tracing in FIG. 4. In the present invention, the negative pressure created by the jet venturi acts to further open the valve, creating the lower pressure vs. flow tracing in FIG. 4. In a ventilator fault condition in which excessive patient pressure is relieved by the ventilator safety valve of the invention, the patient thus experiences lower pressure, thereby reducing the risk of barotrauma.

In addition, the poppet valve seal and diaphragm in combination with the chamber 36 have the ability to dampen oscillations which can otherwise occur in the operation of the ventilator safety valve. The trapped volume in the chamber of the valve housing behaves as an air damper since the only vent for the volume to escape is through the narrow aperture of the poppet valve seal. The valve's mechanical response to an over pressure state, and transient dampening response of the valve can be optimized by adjusting the diameter of the aperture, as desired. The response of the valve can be defined in terms of time to open, and pressure overshoot due to the time required to open.

Referring to FIGS. 1 and 2, a pilot spring 37 is disposed on the shaft between the poppet valve seal diaphragm and a pilot spring adjuster 38 mounted by threads in the valve housing and moveable within the valve housing for adjusting the biasing force of the pilot spring. The pilot spring has a biasing force urging the poppet valve seal to the valve closed position to seal the vent, so that when pressure within the patient airway exceeds the set biasing force of the pilot spring, the poppet valve seal will move to the valve open position to allow relief flow. In a presently preferred embodiment, the shaft extends through the pilot spring adjuster. The valve poppet is thus moved toward and away from the valve opening by movement of the valve poppet shaft longitudinally through the spring adjuster and the housing shaft guide.

A solenoid or electromagnetic coil 40 is also mounted in the valve housing, preferably near the hinge 22 and adjacent to the armature, so that when the electromagnetic coil is energized, the electromagnetic coil exerts a biasing force urging the armature to the armature closed position in which the armature is drawn to the valve housing, as shown in FIG. 1. A return spring 42 is disposed in the valve housing adjacent the other end 44 of the valve housing having a biasing force pushing against the armature, in opposition to the biasing force of the pilot spring and the biasing force of the electromagnetic coil when it is energized. In a presently preferred embodiment, the biasing force of the return spring is less than the biasing force of the electromagnetic coil when energized, and is greater than the biasing force of the pilot spring. The electromagnetic coil will thus allow the poppet valve seal to be moved toward the vent opening by the pilot spring when the electromagnetic coil is energized. Conversely, the return spring will lift the armature, causing the poppet valve seal to move to the valve open position to allow the relief flow, when the electromagnetic coil is not energized, to provide an emergency air pathway for the patient in the event of a ventilator inoperative condition.

To minimize the size and the power consumption of the electromagnetic coil, the opposing forces exerted by the return spring and the pilot spring are preferably determined so as to be near static equilibrium in the valve open configuration. In such a near static equilibrium state, any force produced by the electromagnetic coil acts to bias the valve to close. By positioning the electromagnetic coil adjacent to the hinge, the closing force created by the electromagnetic coil is made stronger. Although the mechanical advantage is reduced proportionally as the solenoid is placed closer to the hinge, the reduced gap distance between the armature and the magnet increases the magnetic strength exponentially.

When the electromagnetic coil is energized, the force created by the electromagnetic coil overcomes the force exerted by the return spring. This force imbalance actuates the valve toward the closed position. In this configuration, the pneumatic and electromechanical portion of the valve are uncoupled, allowing the valve to relieve pressure by the mechanics of a force balance between the patient pressure and the pilot spring.

The pressure relief action of the valve is enhanced by the aperture in the poppet valve seal and the diaphragm sealing element of the valve. When the valve is relieving pressure, the flow across the poppet valve seal creates a jet venturi effect resulting in a negative pressure that biases the valve to open further. Consequently, the steady-state pressure is low when the valve is permitting relief flow at high flow rates.

When the electromagnetic coil is de-energized, the force exerted by the return spring overcomes the opposing force of the pilot spring, actuating the valve to open. In this configuration, the electromechanical assembly is coupled to the pneumatic hardware and negates the pneumatic function of the valve. It is through this mechanism that the safety valve provides an emergency vent during an event of a power failure. During normal ventilation, the electromagnetic coil is energized and the safety valve remains in pressure relief mode. If power is interrupted for any reason, the safety valve functions as a vent port.

It has thus been demonstrated that the ventilator safety valve of the invention functions to relieve patient pressure in excess of a predetermined level during ventilator operation, and provides an emergency path for the patient to breathe in the absence of electrical power to the safety valve. In addition, while in conventional spring-operated pressure relief valves, pressure is generally proportional to the relief valve flow, so that the pressure experienced by the patient will increase with the flow rate during pressure relief, the ventilator safety valve of the invention utilizes a jet venturi effect created by an aperture in the poppet valve seal so that the negative pressure created by the jet venturi acts to further open the valve during flow relief. In a ventilator fault condition in which the ventilator safety valve opens in response to a high pressure condition in the patient airway to permit relief flow, the patient experiences further reduced pressure, thereby reducing the risk of barotrauma. Furthermore, the trapped volume on the opposing side of the poppet valve seal provides an air damper since the only vent for the volume to escape is through the orifice. Also, the response of the valve can be adjusted by varying the size of the orifice.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A lung ventilator safety valve for relieving pressure from a vent in a patient airway of a ventilator system, said safety valve having a valve open position venting pressure from the patient airway and a valve closed position, and said safety valve comprising:

a valve housing fluidly connected to a vent having a valve seat in the patient airway;

a poppet valve seal mounted adjacent to the valve seat of the vent for allowing a relief flow from the vent in the valve open position and for sealing the vent in the valve closed position;

a pilot spring urging said poppet valve diaphragm to the valve closed position to seal the vent, whereby said poppet valve seal will move to the valve open position to allow the relief flow when pressure within the patient airway exceeds the biasing force of the pilot spring, to protect a patient from excess pressure in the patient airway;

an electromagnetic coil mounted to said valve housing, said electromagnetic coil when energized urging said valve to the valve closed position; and a return spring disposed in said valve housing opposing said pilot spring and the electromagnetic coil when energized, whereby said electromagnetic coil allows said poppet valve seal to move to the valve closed position when said electromagnetic coil is energized, and said return spring causes said poppet valve seal to move to the valve open position to allow the relief flow when said electromagnetic coil is not energized, to provide an emergency air pathway for a patient in the event of interruption of power to the ventilator.

2. The lung ventilator safety valve of claim 1, wherein said poppet valve seal comprises a flexible diaphragm extending to the valve housing around the poppet valve seal forming a chamber in the valve housing.

3. The lung ventilator safety valve of claim 1, wherein the surface of the poppet valve seal defines an aperture extending through the poppet valve seal, whereby when there is relief flow through the safety valve vent, the relief flow across the valve poppet diaphragm creates a venturi effect resulting in a negative pressure on the opposing side of the diaphragm that biases the safety valve to open further.

4. The lung ventilator safety valve of claim 1, further comprising a pilot spring adjuster disposed in said valve housing adjacent to said pilot spring for adjusting the biasing force of the pilot spring.

5. The lung ventilator safety valve of claim 4, further comprising a shaft disposed in said valve housing, and wherein said shaft extends through said pilot spring adjuster.

6. The lung ventilator safety valve of claim 1, further comprising an armature connected to the valve housing by a hinge, and wherein said electromagnetic coil is mounted adjacent to the hinge.

* * * * *